(12) United States Patent
Clayton

(10) Patent No.: US 12,005,274 B2
(45) Date of Patent: Jun. 11, 2024

(54) HIGH DOSE RATE RADIOTHERAPY, SYSTEM AND METHOD

(71) Applicant: Varian Medical Systems, Inc., Palo Alto, CA (US)

(72) Inventor: James Clayton, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 106 days.

(21) Appl. No.: 17/697,430

(22) Filed: Mar. 17, 2022

(65) Prior Publication Data

US 2023/0293909 A1   Sep. 21, 2023

(51) Int. Cl.
| | |
|---|---|
| *A61N 5/10* | (2006.01) |
| *G21K 1/093* | (2006.01) |
| *G21K 1/10* | (2006.01) |
| *H01J 35/08* | (2006.01) |
| *H01J 35/10* | (2006.01) |
| *H01J 35/14* | (2006.01) |

(Continued)

(52) U.S. Cl.
CPC ......... *A61N 5/1077* (2013.01); *A61N 5/1043* (2013.01); *A61N 5/1045* (2013.01); *A61N 5/1047* (2013.01); *A61N 5/1081* (2013.01); *G21K 1/093* (2013.01); *G21K 1/10* (2013.01); *H01J 35/10* (2013.01); *H01J 35/116* (2019.05); *H01J 35/153* (2019.05); *H01J 35/22* (2013.01); *H01J 35/30* (2013.01); *H05G 2/00* (2013.01); *H05H 9/048* (2013.01); *A61N 2005/1089* (2013.01)

(58) Field of Classification Search
CPC ...... A61N 5/10; A61N 5/1042; A61N 5/1043; A61N 5/1045; A61N 5/1047; A61N 5/1077; A61N 5/1081; A61N 2005/1089; A61N 2005/1091; H01J 35/02; H01J 35/025; H01J 35/06; H01J 35/08; H01J 35/10; H01J 35/101; H01J 35/112; H01J 35/116; H01J 35/14; H01J 35/147; H01J 35/153; H01J 35/18; H01J 35/186; H01J 35/22; H01J 35/24; H01J 35/26; H01J 35/30; H01J 35/305; H05H 9/02; H05H 9/04; H05H 9/048
USPC .......... 378/65, 137, 138, 143, 144; 313/505
See application file for complete search history.

(56) References Cited

U.S. PATENT DOCUMENTS

| | | | | | |
|---|---|---|---|---|---|
| 4,229,657 | A | * | 10/1980 | Bensussan | ............. H01J 35/30 378/143 |
| 4,442,352 | A | * | 4/1984 | Brahme | ................... G21K 5/04 250/493.1 |

(Continued)

OTHER PUBLICATIONS

Bjorn Andreassen; et al. Development of an efficient scanning and purging magnet system for IMRT with narror high energy photon beams. Journal. (2009) 201-208; 6 pp.

*Primary Examiner* — Allen C. Ho
(74) *Attorney, Agent, or Firm* — Harness, Dickey & Pierce, P.L.C.

(57) ABSTRACT

A radiotherapy system includes an X-ray target configured to convert an incident electron beam into a therapeutic X-ray beam, a purging magnet configured to redirect unwanted particles emitted from the X-ray target away from the therapeutic X-ray beam, and a particle collector configured to absorb the unwanted particles subsequent to redirection by the purging magnet. The particle collector may be configured to dissipate at least 50% of the energy of the incident electron beam.

24 Claims, 7 Drawing Sheets

(51) Int. Cl.
*H01J 35/22* (2006.01)
*H01J 35/30* (2006.01)
*H05G 2/00* (2006.01)
*H05H 9/00* (2006.01)
*H05H 9/04* (2006.01)

(56) References Cited

U.S. PATENT DOCUMENTS

| | | | | |
|---|---|---|---|---|
| 4,845,371 A * | 7/1989 | Stieber | ............ | G21K 1/02 |
| | | | | 976/DIG. 428 |
| 5,663,999 A * | 9/1997 | Siochi | ............ | A61N 5/1042 |
| | | | | 378/65 |
| 6,332,017 B1 * | 12/2001 | Carroll | ............ | H05G 2/00 |
| | | | | 378/138 |
| 6,407,505 B1 * | 6/2002 | Bertsche | ............ | H05H 9/04 |
| | | | | 315/5.46 |
| 6,493,424 B2 * | 12/2002 | Whitham | ............ | H05H 9/04 |
| | | | | 378/65 |
| 6,687,333 B2 * | 2/2004 | Carroll | ............ | H05G 2/00 |
| | | | | 378/138 |
| 7,630,474 B2 | 12/2009 | Clayton | | |
| 7,826,593 B2 * | 11/2010 | Svensson | ............ | A61N 5/1042 |
| | | | | 378/65 |
| 8,232,748 B2 * | 7/2012 | Treas | ............ | H05H 7/02 |
| | | | | 250/397 |
| 8,306,184 B2 * | 11/2012 | Chang | ............ | A61N 5/103 |
| | | | | 378/65 |
| 8,311,187 B2 * | 11/2012 | Treas | ............ | H01J 35/16 |
| | | | | 315/505 |
| 9,079,027 B2 * | 7/2015 | Agano | ............ | A61N 5/1077 |
| 9,167,681 B2 * | 10/2015 | Cheung | ............ | H05H 9/02 |
| 9,258,876 B2 * | 2/2016 | Cheung | ............ | H05H 7/02 |
| 9,844,358 B2 * | 12/2017 | Wiggers | ............ | A61B 6/588 |
| 10,636,609 B1 * | 4/2020 | Bertsche | ............ | A61N 5/1081 |
| 10,880,984 B2 * | 12/2020 | Kroc | ............ | H05H 7/04 |
| 11,007,381 B2 * | 5/2021 | Purwar | ............ | A61N 5/103 |
| 11,058,893 B2 * | 7/2021 | Boyd | ............ | A61N 5/1049 |
| 11,291,104 B2 * | 3/2022 | Kroc | ............ | H05H 7/04 |
| 11,559,703 B2 * | 1/2023 | Shaw | ............ | A61N 5/1042 |
| 11,717,584 B2 * | 8/2023 | Kroc | ............ | G21K 5/02 |
| | | | | 250/396 ML |
| 11,724,127 B2 * | 8/2023 | Constantin | ............ | A61N 5/1031 |
| | | | | 250/492.3 |

* cited by examiner

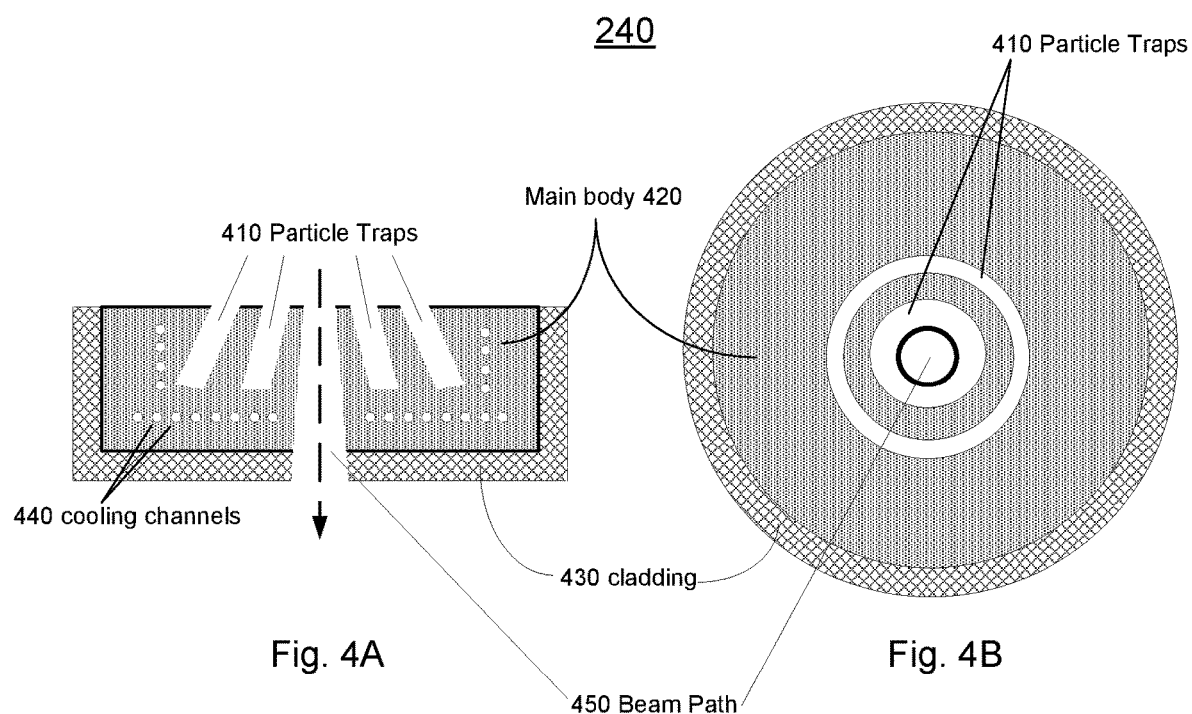

HIGH DOSE RATE RADIOTHERAPY, SYSTEM AND METHOD

FIELD OF INVENTION

Embodiments of the present invention relate to the field of medical devices. More specifically, embodiments of the present invention relate to systems and methods for high dose rate radiotherapy.

BACKGROUND

External beam radiation therapy may be used in the treatment of various cancers and non-malignant conditions. Generally, ionizing radiation, including, for example, photons, e.g., X-rays, gamma rays, and charged particles, e.g., protons and electrons, is directed at an area of interest. In many cases, such ionizing radiation is generated by a linear accelerator or a cyclotron.

FLASH radiotherapy is an emerging radiotherapy regime that appears to reduce radiation-induced toxicities while maintaining a tumor response similar to that of more conventional radiotherapy regimes. FLASH radiotherapy may be characterized as delivering a high radiation rate, e.g., greater than about 40 Grays (Gy) per second, that allows for a total radiotherapy treatment dose, or large fractions of a total radiation dose, to be delivered in parts of a second, compared to several minutes for conventional radiotherapy. For example, a conventional radiotherapy treatment may include a total dose of 12-25 grays (Gy) delivered at a rate of up to 0.4 Gy/s, requiring minutes of treatment time. In contrast, FLASH radiotherapy may deliver a similar total dose at a rate of 40 Gy/s, requiring a fraction of a second of treatment time.

However, generating such high dosage radiotherapy requires an increase in instantaneous dose rates of several orders of magnitude in comparison to conventional instantaneous dose rates. For example, an instantaneous dose rate of FLASH radiotherapy may be 100 times or more higher than an instantaneous dose rate used in conventional radiotherapy. For FLASH photon (X-ray) radiotherapy, this requires corresponding increases in the electron currents impacting an X-ray target. Unfortunately, conventional X-ray targets and associated components are not suitable for the large currents and/or instantaneous dose rates characteristic of FLASH radiotherapy. For example, if exposed to the high beam currents and/or instantaneous dose rates characteristic of FLASH radiotherapy, conventional X-ray targets may deteriorate and/or be destroyed. In addition, repeated thermal cycling, e.g., heating and cooling, of conventional X-ray targets may cause such conventional X-ray targets to crack and/or melt due to thermal stresses.

SUMMARY OF THE INVENTION

Therefore, what is needed are systems and methods for high dose rate radiotherapy. What is additionally needed are systems and methods for high dose rate radiotherapy that remain reliable in response to the high power levels of X-ray FLASH radiotherapy. Further, there is a need for systems and methods for high dose rate electron beam therapy that allow for scanning of a radiotherapy beam. There is a further need for systems and methods for high dose rate electron beam therapy that are compatible and complementary with existing systems and methods of administering radiotherapy.

In accordance with an embodiment of the present invention, a radiotherapy system includes an X-ray target configured to convert an incident electron beam into a therapeutic X-ray beam, a purging magnet configured to redirect unwanted particles emitted from the X-ray target away from the therapeutic X-ray beam, and a particle collector configured to absorb the unwanted particles subsequent to redirection by the purging magnet. The particle collector is configured to dissipate at least 50% of the energy of the incident electron beam.

According to another embodiment, a radiotherapy system configured for FLASH radiotherapy includes a linear accelerator configured to accelerate a stream of electrons to an energy of, for example, at least 50 MeV. Embodiments in accordance with the present invention are well-suited to lower electron energies, as well. The system also includes a bremsstrahlung X-ray target configured to convert a portion of the stream of electrons into X-rays, and a purging magnet configured to redirect residual particles escaping from the bremsstrahlung X-ray target while passing the X-rays; and a particle collector configured to absorb the escaping particles subsequent to redirection by the purging magnet.

In accordance with a method embodiment of the present invention, a method of operating a radiotherapy system includes impinging an electron beam on an X-ray target. The X-ray target includes refractory metals. The method additionally includes redirecting unwanted particles out of a therapeutic X-ray beam by a purging magnet, and absorbing the unwanted particles, e.g., electrons, by a particle collector. The particle collector includes lower-Z materials to minimize X-ray production by the particle collector.

BRIEF DESCRIPTION OF THE DRAWINGS

The accompanying drawings, which are incorporated in and form a part of this specification, illustrate embodiments of the invention and, together with the description, serve to explain the principles of the invention. Unless otherwise noted, the drawings may not be drawn to scale.

FIG. 4A illustrates a side sectional view of an exemplary particle collector, in accordance with embodiments of the present invention.

FIG. 4B illustrates a plan view of an exemplary particle collector, in accordance with embodiments of the present invention.

DETAILED DESCRIPTION

Figure 1:
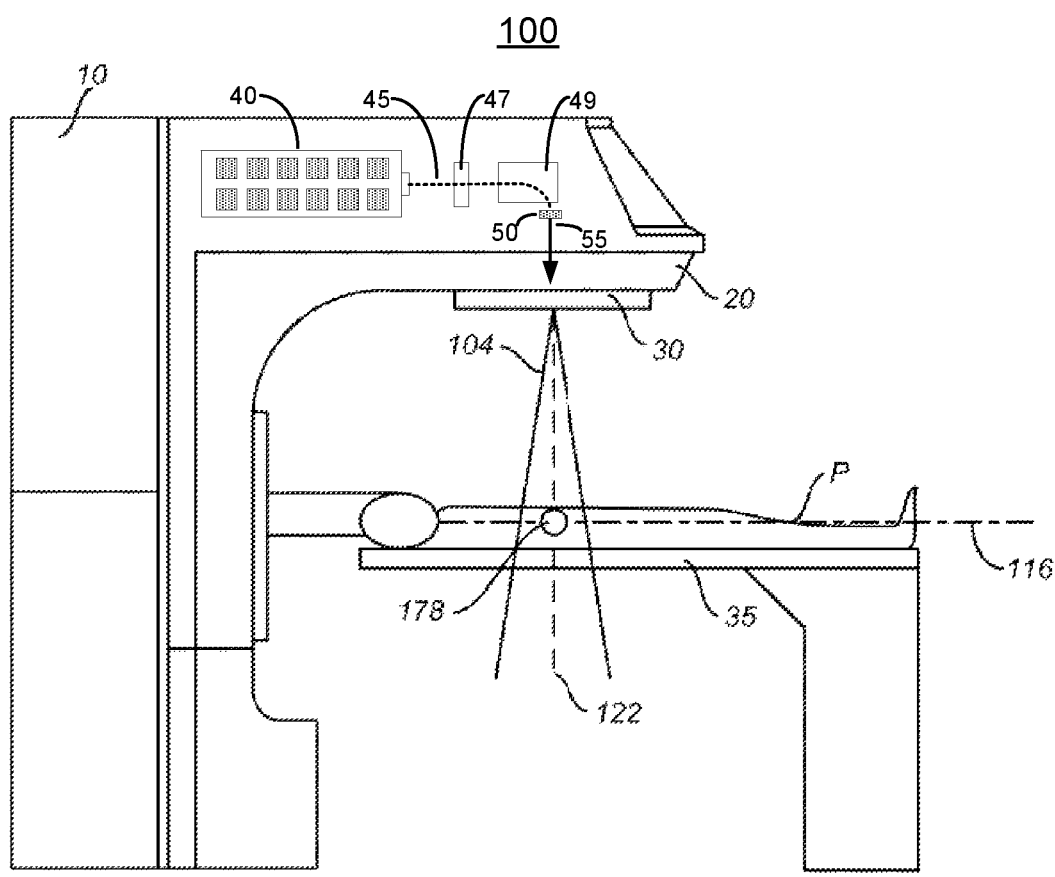
FIG. 1 illustrates a block diagram of an exemplary radiation treatment system that may serve as a platform for embodiments in accordance with the present invention.

Reference will now be made in detail to various embodiments of the invention, examples of which are illustrated in the accompanying drawings. While the invention will be described in conjunction with these embodiments, it is understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the invention, numerous specific details are set forth in order to provide a thorough understanding of the invention. However, it will be recognized by one of ordinary skill in the art that the invention may be practiced without these specific details. In other instances, well known methods, procedures, components, and circuits have not been described in detail as not to unnecessarily obscure aspects of the invention.

Some portions of the detailed descriptions which follow (e.g., method 500) are presented in terms of procedures, steps, logic blocks, processing, and other symbolic representations of operations on data bits that may be performed on computer memory. These descriptions and representations are the means used by those skilled in the data processing arts to most effectively convey the substance of their work to others skilled in the art. A procedure, computer executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, data, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "applying" or "controlling" or "generating" or "testing" or "heating" or "bringing" or "capturing" or "storing" or "reading" or "analyzing" or "resolving" or "accepting" or "selecting" or "determining" or "displaying" or "presenting" or "computing" or "sending" or "receiving" or "reducing" or "detecting" or "setting" or "accessing" or "placing" or "forming" or "mounting" or "removing" or "ceasing" or "stopping" or "coating" or "processing" or "performing" or "adjusting" or "creating" or "executing" or "continuing" or "indexing" or "translating" or "calculating" or "measuring" or "gathering" or "running" or the like, refer to the action and processes of, or under the control of, a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The meaning of "non-transitory computer-readable medium" should be construed to exclude only those types of transitory computer-readable media which were found to fall outside the scope of patentable subject matter under 35 U.S.C. § 101 in *In re Nuijten*, 500 F.3d 1346, 1356-57 (Fed. Cir. 2007). The use of this term is to be understood to remove only propagating transitory signals per se from the claim scope and does not relinquish rights to all standard computer-readable media that are not only propagating transitory signals per se.

In the following disclosure, exemplary embodiments in accordance with the present invention are illustrated in terms of a linear accelerator and radiotherapy photons, e.g., X-rays. However, it will be appreciated by those skilled in the art that the same or similar principles apply to other systems, including, for example, cyclotrons, and other types of ionizing radiation, including, for example, photons, e.g., X-rays, electrons, protons, and/or other particles. All such systems are well suited to, and are within the scope of embodiments in accordance with the present invention.

In the following descriptions, various elements and/or features of embodiments in accordance with the present invention are presented in isolation so as to better illustrate such features and as not to unnecessarily obscure aspects of the invention. It is to be appreciated, however, that such features, e.g., as disclosed with respect to a first drawing, may be combined with other features disclosed in other drawings in a variety of combinations. All such embodiments are anticipated and considered, and may represent embodiments in accordance with the present invention.

High Dose Rate Radiotherapy, System and Method

FIG. 1 illustrates a block diagram of an exemplary radiation treatment system 100 that may serve as a platform for embodiments in accordance with the present invention. Radiation treatment system 100 may be similar to a TrueBeam® radiotherapy system, commercially available from Varian Medical Systems, Palo Alto, CA.

Stand 10 supports a rotatable gantry 20 with a treatment head 30. The treatment head 30 may extend into the gantry 20. In proximity to stand 10 there is arranged a control unit (not shown) which includes control circuitry for controlling the different modes of operation of the system 100.

Radiation treatment system 100 comprises a linear accelerator 40, for example, within gantry 20, utilized to create a radiation beam. Typically, radiation treatment system 100 is capable of generating either an electron (particle) beam or an X-ray (photon) beam for use in the radiotherapy treatment of patients on a treatment couch 35. Other radiation treatment systems are capable of generating light ion particles such as protons, alpha particles, or carbon ions. For purposes of the following disclosure, only X-ray (photon) irradiation will be discussed.

A high voltage source is provided within the stand and/or in the gantry to supply voltage to an electron gun (not shown) positioned on an accelerator guide located in the gantry 20. Electrons are emitted from the electron gun into the accelerator 40 where they are accelerated. A source supplies radio frequency (microwave) power for the generation of an electric field within the waveguide. The electrons emitted from the electron gun are accelerated in the waveguide by the electric field, and exit the waveguide as a high-energy electron beam 45, for example, at megavoltage energies. The electron beam 45 may pass through a set of bending plane scan magnets 47, in some embodiments. The electron beam 45 may pass through a set of bend magnets 49, to redirect the electron beam 45 from substantially horizontal to substantially vertical, in some embodiments. The electron beam 45 then strikes a suitable X-ray target 50, for example, a bremsstrahlung transmission target, converting a portion of the electron beam 45 into X-rays (photons) 55 in the direction of a patient P.

As illustrated in FIG. 1, a patient P is shown lying on the treatment couch 35. High energy photons as described above are emitted from the treatment head 30 in a divergent beam 104. Typically, a patient plane 116, is positioned, for example, about one meter from the X-ray target 50, and the rotational axis of the gantry 20 is located on the patient plane 116, such that the distance between the X-ray target 50 and the isocenter 178 remains constant when the gantry 20 is rotated. It is appreciated that for photon FLASH therapy, the patient plane 116 may be less than one meter from the electron gun. The isocenter 178 is at the intersection between the axis of rotation of the gantry 20 and the central axis 122 of the divergent beam 104. A treatment volume to be irradiated may be located about the isocenter 178, or in some embodiments may be located closer to or farther from the treatment head 30. It is appreciated that some treatment plans may utilize a primary treatment target that is off of the central axis 122 of the divergent beam 104, and such arrangements are within the scope of embodiments in accordance with the present invention.

Figure 2:
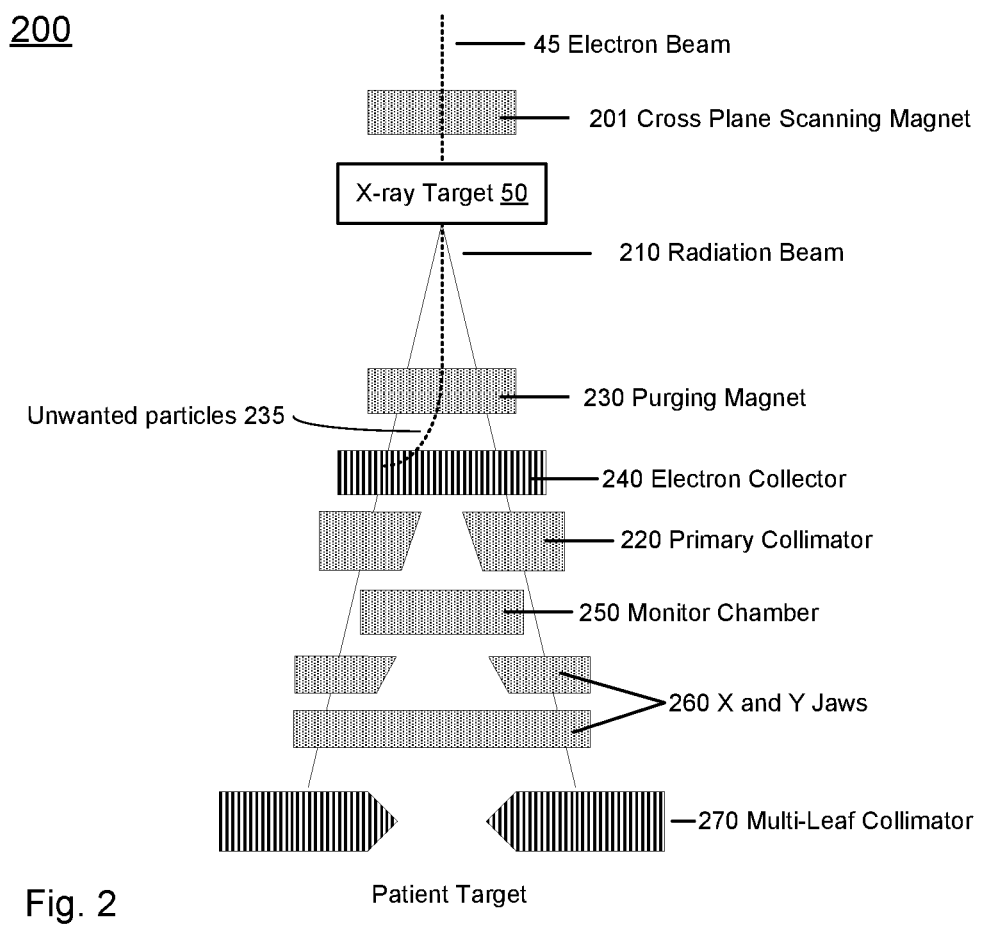
FIG. 2 illustrates a side-sectional schematic representation of an exemplary beam path within an exemplary radiation treatment system, in accordance with embodiments of the present invention.

FIG. 2 illustrates a side-sectional schematic representation of an exemplary beam path 200 within exemplary radiation treatment system 100, in accordance with embodiments of the present invention. It is appreciated that the illustrated components of beam path 200 are exemplary, and all may not be required in some embodiments. Additional components, e.g., a flattening filter (not shown), may also be included in accordance with embodiments of the present invention. Prior to impinging X-ray target 50, electron beam 45 may pass through a set of cross plane scanning magnets 201, in some embodiments. As previously presented, electron beam 45 impinges on X-ray target 50 producing X-ray radiation beam 210. Radiation beam 210 passes through purging magnet 230. Purging magnet 230 functions to redirect unwanted particles 235, for example, electrons and/or positrons, that pass through and/or are produced by X-ray target 50.

Radiation beam 210 passes through a monitor chamber 250, sometimes known or referred to as an "ion chamber." Monitor chamber 250 functions to measure a radiotherapy dose. The X and Y jaws 260, and the leaves of the multi-leaf collimator (MLC) 270 function to shape radiation beam 210 to a desired shape and/or beam profile for patient treatment.

The primary collimator 220 may comprise a plurality of selectable collimators and/or filters, in some embodiments. The primary collimator 220, typically comprises an X-ray blocking material, and may be positioned in the head 30 (FIG. 1) to define the width of the X-ray beam at the patient plane. Typically, the X and Y jaws 260 are moveable and, when fully open, define a maximum beam width at the patient plane 116 (FIG. 1). The MLC 270 may be positioned at the exit of the head 30, to further shape the X-ray beam. Exemplary MLCs may use up to 120 individually controllable leaves, for example, thin slices of tungsten, which may be moved into or out of the X-ray beam under the control of system software.

Particle collector 240 functions to capture and/or absorb the unwanted particles 235 redirected by purging magnet 230.

Under the conventional art, an X-ray target is designed to absorb substantially all of the energy of an incident electron beam. For example, most of the incident electrons lose all of their energy in the target. Such conventional X-ray targets may be damaged or destroyed when subjected to the significantly higher electron beam power corresponding to FLASH radiotherapy. In accordance with embodiments of the present invention, an X-ray target for FLASH radiotherapy is part of a system that does not require the X-ray target to absorb all of the energy of an incident electron beam.

In accordance with embodiments of the present invention, X-ray target 50 is relatively thin, e.g., less than about 3.5 mm thick, and comprises refractory metals. Refractory metals are characterized as a high Z materials, e.g., materials comprising elements with a high atomic number ("Z") of protons in the nucleus, and having a high melting temperature. As used herein, "high-Z" refers to or describes elements having an atomic number of 42, corresponding to molybdenum (Mo), or greater. Exemplary elements include tungsten (W), tantalum (Ta), molybdenum (Mo), gold (Au), and/or antimony (Sb). The thickness of X-ray target 50 is selected to be sufficient to generate the required dose of X-rays, while minimizing attenuation and energy loss of the incident high-energy electrons. Exemplary thicknesses may range from about 1.5 mm to 3.5 mm for an X-ray target 50 comprising tungsten (W). As attenuation of high-energy electrons within the X-ray target 50 produces heat, minimizing such electron attenuation beneficially decreases the amount of heat that X-ray target 50 must endure and/or be removed from X-ray target 50. Reducing heating of X-ray target 50 is critical to the stability and reliability of a FLASH radiotherapy system.

It is appreciated that X-ray target 50, while designed to limit heat production/absorption, may still be required to dissipate large amounts of heat, e.g., on the order of kilowatts, in FLASH radiotherapy applications. Accordingly, the X-ray target 50 may require heat transfer systems typically not found in conventional radiotherapy applications. Such systems may include, for example, flowing a liquid cooling medium, for example, water or liquid metal, e.g., gallium (Ga), over the emitting surface of the X-ray target 50, coupling cooling fins to X-ray target 50, coupling X-ray target 50 to coolant loops and/or Peltier devices, and the like.

As an unfortunate result of designing X-ray target 50 to minimize heating due to high energy electrons while producing enough X-rays for the desired FLASH radiotherapy regime, the radiation beam emitted from X-ray target 50 may include undesirable or unwanted particles 235, including, for example, electrons and/or other charged particles, e.g., protons, that pass through and/or are created by X-ray target 50. Such unwanted particles 235 should not radiate a patient. In addition, such unwanted particles 235 may comprise a majority of the energy of electron beam 45.

In accordance with embodiments of the present invention, a purging magnet 230 functions to redirect such unwanted particles 235 into particle collector 240. Purging magnet 230 is generally located immediately adjacent to an X-ray target, and subsequent to such an X-ray target along a radiation path. Purging magnet 230 may comprise multiple magnets of any suitable type, including, for example, electro-magnets, permanent magnets, rare-earth magnets, cryogenic magnets, and the like. Purging magnet 230 may comprise trimming magnets, e.g., "trim coils," to adjust an overall magnetic field strength and/or magnetic field shape of purging magnet 230, in some embodiments. Purging magnet 230 may be moveable, for example, to modify a deflection of unwanted particles 235, in some embodiments. A magnetic field strength of purging magnet 230 may be changeable, for example, to modify a deflection of unwanted particles 235, in some embodiments. Purging magnet 230 may comprise multiple poles, in some embodiments. In some embodiments, magnetic field strength of purging magnet 230, relative magnetic field strength of multiple magnetic poles, and/or a location of purging magnet 230 may be changed in coordination with operations of scanning magnets, e.g., cross plane scanning magnets 201 and/or bending plane scan magnets 47 (FIG. 1).

Particle collector 240 functions to absorb unwanted particles 235. Particle collector 240 is generally located immediately adjacent to a purging magnet, e.g., purging magnet 230, and subsequent to such a purging magnet along a radiation path. It is appreciated that particle collector 240 absorbs the majority of energy of the electron beam 45.

For example, an exemplary FLASH radiotherapy treatment may require an electron energy of at least 50 MeV, producing up to 25 kW of average beam power. The X-ray target 50 may be required to dissipate only 5 kW of this average beam power, while the particle collector 240 dissipates the remaining 20 kW of average beam power.

Figure 3A:
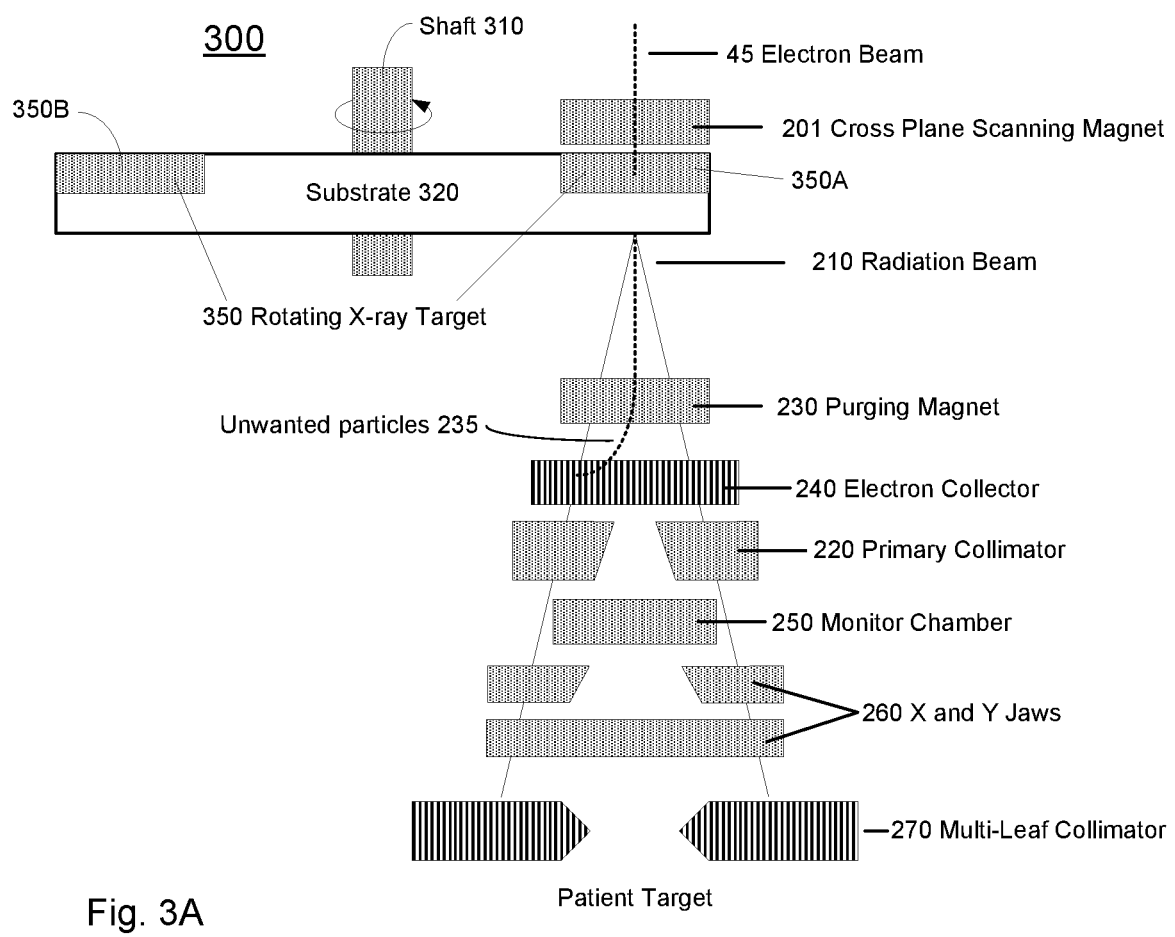
FIG. 3A illustrates a side-sectional schematic representation of an exemplary beam path within an exemplary radiation treatment system, in accordance with embodiments of the present invention.

FIG. 3A illustrates a side-sectional schematic representation of an exemplary beam path 300 within exemplary radiation treatment system 100, in accordance with embodiments of the present invention. Beam path 300 comprises a rotating X-ray target 350. In accordance with embodiments of the present invention, rotating X-ray target 350 is configured to rotate through electron beam 45. For example, at a first time, a first portion of rotating X-ray target 350 is in the path of electron beam 45. At a second time, the first portion of rotating X-ray target 350 is no longer in the path of electron beam 45, and a second portion of rotating X-ray target 350 is in the path of electron beam 45.

Rotating X-ray target 350 may be mounted onto or within a rotating substrate 320, in some embodiments. Rotating substrate 320, if present, is configured to mechanically support rotating X-ray target 350 at rest and during rotation. Rotating substrate 320, if present, should comprise materials that do not interfere with electron beam 45 and/or radiation beam 210. Rotating substrate 320, if present, may help to conduct heat away from rotating X-ray target 350, in some embodiments. Some embodiments in accordance with the present invention may not require a rotating substrate 320. For example, rotating X-ray target 350 may be self-supporting.

Rotating X-ray target 350 may comprise an annular ring shape, in some embodiments. Rotating X-ray target 350 may form a disk, in some embodiments. Rotating X-ray target 350 and rotating substrate 320, if present, are configured to rotate on a shaft 310 in either direction, e.g., clockwise or counter clockwise in plan view. Exemplary rotation rates may range from 10-1000 RPM, in some embodiments.

Rotating X-ray target 350 may comprise comparable materials and thickness, e.g., a vertical dimension in the view of FIG. 3A, to X-ray target 50, as described with respect to FIG. 2, in some embodiments. It is appreciated that rotating X-ray target 350 is configured to operate in a transmission mode, as opposed to a reflection mode.

It is appreciated that only a portion of rotating X-ray target 350 is irradiated by electron beam 45 at any given instant of time. As illustrated in FIG. 3A, a portion 350A is subjected to electron beam 45. The majority of rotating X-ray target 350 is not irradiated by electron beam 45 at any given instant of time. For example, portion 350B is illustrated as outside the path of electron beam 45, and is not presently irradiated.

When portion 350A is subjected to electron beam 45, the portion 350A generates radiation beam 210, as previously described with respect to X-ray target 50 (FIG. 2). When subjected to electron beam 45, the portion 350A heats up. Meanwhile, the portion 350B is not impinged by electron beam 45, and is not subject to electron-induced heating. By rotating the rotating X-ray target 350, portions 350A and 350B move into and out of electron beam 45.

In accordance with embodiments of the present invention, portions of rotating X-ray target 350, e.g., portion 350B, that are not impacted by electron beam 45 may be cooled by any suitable passive and/or active cooling processes. Active cooling processes may include, for example, using a cooling fluid, e.g., air, ammonia, other refrigerants, water, and/or liquid metal, etc., to transfer heat away from portion 350B. Portion 350A may have active cooling applied, for example as described with respect to X-ray target 50 (FIG. 2), in some embodiments. In accordance with embodiments of the present invention, portions 350A and 350B may be cooled by different combinations of cooling processes. Some cooling processes may be common to both portions 350B and 350A.

In accordance with embodiments of the present invention, rotating X-ray target 350 absorbs less heat per cross sectional volume than is absorbed by X-ray target 50 (FIG. 2), for comparable electron beam 45 currents. For example, a given volume of X-ray target 350 is only exposed to electron beam 45 for a brief time interval, and then is rotated out of the beam, decreasing time of exposure to electron beam 45 for any given portion, and thus decreasing total dose of electron beam 45 for any given portion. Accordingly, in some embodiments, rotating X-ray target 350 may be designed to attenuate a greater percentage of electron beam 45 in comparison to X-ray target 50. Advantageously, rotating X-ray target 350 may be thicker in comparison to X-ray target 50, and may be more efficient at converting electrons into the desired X-rays in comparison to X-ray target 50.

Figure 3B:
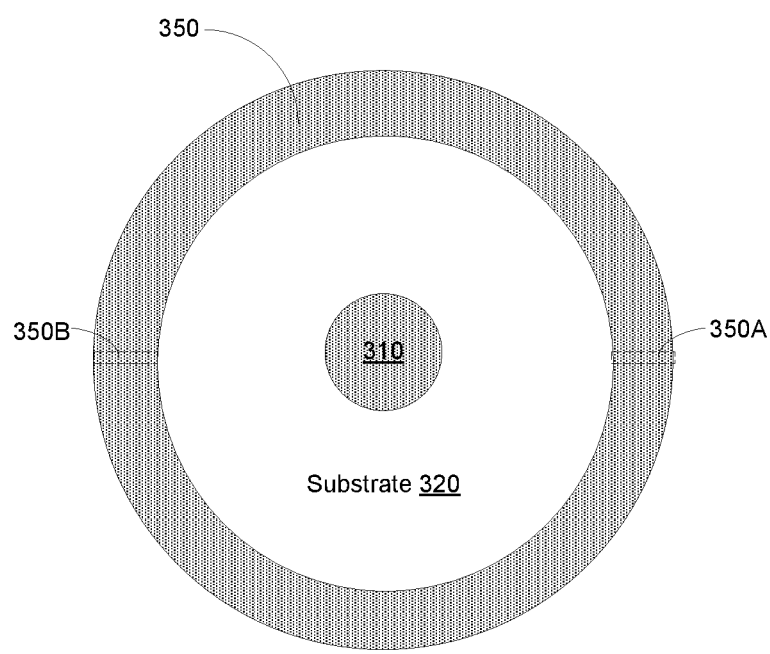
FIG. 3B illustrates a plan view of an exemplary X-ray target, in accordance with embodiments of the present invention.

FIG. 3B illustrates a plan view of an exemplary rotating X-ray target 350, in accordance with embodiments of the present invention. The rotating X-ray target 350 is illustrated as an annular ring, although that is not required. The width of such an annular ring may be wider than a footprint of electron beam 45 upon the rotating X-ray target 350.

FIG. 4A illustrates a side sectional view of an exemplary particle collector 240, in accordance with embodiments of the present invention. Particle collector 240 functions to absorb and/or contain unwanted particles 235 while passing desired photons (X-rays) to a patient. It is appreciated that particle collector 240 absorbs a majority of the energy of electron beam 45, and transfers that energy as heat out of the radiotherapy system.

Particle collector 240 comprises a main body 420. Main body 420 is configured to contain, absorb, and dissipate a majority of the energy of electron beam 45. Main body 420 may comprise low Z materials, selected to minimize X-ray production and maximize heat transfer. As used herein, "low-Z" refers to or describes elements having an atomic number of less than 42, corresponding to molybdenum (Mo). Exemplary materials include copper (Cu) and aluminum (Al). Main body 420 may comprise pure materials, alloys, amalgams, and/or non-metals, including, for example, ceramics, in some embodiments. Main body 420 may be characterized as homogeneous or non-homogeneous, in some embodiments.

Particle collector 240 may comprise a shield or cladding 430, in accordance with embodiments of the present invention. Cladding 430 functions to prevent any unwanted particles 235, or other particles, from escaping particle collector 240. Cladding 430 also functions to prevent any X-rays generated by particle collisions within main body 420 from escaping particle collector 240. In embodiments, cladding 430 comprises radiation absorbing materials, e.g., lead (Pb), tungsten (W), and/or lead-antimony (Pb—Sb). Cladding 430 may comprise pure materials, alloys, amalgams, and/or non-metals, including, for example, ceramics, in some embodiments. Cladding 430 may be characterized as homogeneous or non-homogeneous, in some embodiments. Cladding 430 may comprise multiple layers of different materials, in some embodiments. For example, cladding 430 may comprise an inner layer of tungsten (W) and an outer layer of lead (Pb) or lead/antimony (Pb—Sb). Steel may also be used for structural integrity, in embodiments.

Particle collector 240 may typically comprise a plurality of cooling channels 440, configured to increase a cooling capacity of particle collector 240. The illustrated number, location and shape of cooling channels 440 are exemplary. Cooling channels 440 are configured to conduct a cooling fluid, e.g., liquid and/or gas, to absorb heat from particle collector 240 to be dissipated externally, for example, in a radiator and/or chiller. Cooling channels 440 may be part of a phase-change cooling system, in some embodiments. Cooling channels 440 may be formed in main body 420 and/or cladding 430, in some embodiments.

Particle collector 240 generally comprises a plurality of particle traps 410. The number and location of particle traps illustrated is exemplary, and embodiments in accordance with the present invention are well suited to other quantities and locations of particle traps. Particle traps 410 are configured to align with the path(s) of unwanted particles 235 as deflected by purging magnet 230. Particle traps 410 are also configured to increase a surface area of particle collector 240 to increase absorption of unwanted particles 235 and increase radiative cooling. The illustrated shapes of particle traps 410 are exemplary.

Particle collector 240 generally comprises a beam path 450 configured to allow therapeutic photons (X-rays) to pass through particle collector 240 substantially unabated. Beam path 450 may comprise a void, or may comprise materials, e.g., low density materials, with low absorption characteristics for the desired radiotherapy X-rays.

FIG. 4B illustrates a plan view of an exemplary particle collector 240, in accordance with embodiments of the present invention. The illustrated plan shape is exemplary. Embodiments in accordance with the present invention are well suited to a variety of regular or non-regular plan shapes for particle collector 240. Particle taps 410 are generally designed to correspond with a pattern of deflected particles produced by purging magnets 230, and may be any suitable shape. Similarly, beam path 450 is generally designed to correspond to a desired photon (X-ray) radiation pattern. It is appreciated that numerous devices and/or operations of a radiotherapy system function to shape a radiotherapy beam, for example, X-ray target 50, primary collimator 220 (FIG. 2), X and Y jaws 260 (FIG. 2), multi-leaf collimator 270 (FIG. 2), cross plane scanning magnets 201 (FIG. 2), and/or bending plane scan magnets 47 (FIG. 1). A shape of beam path 450 may generally account for all such beam shaping elements.

Figure 5:
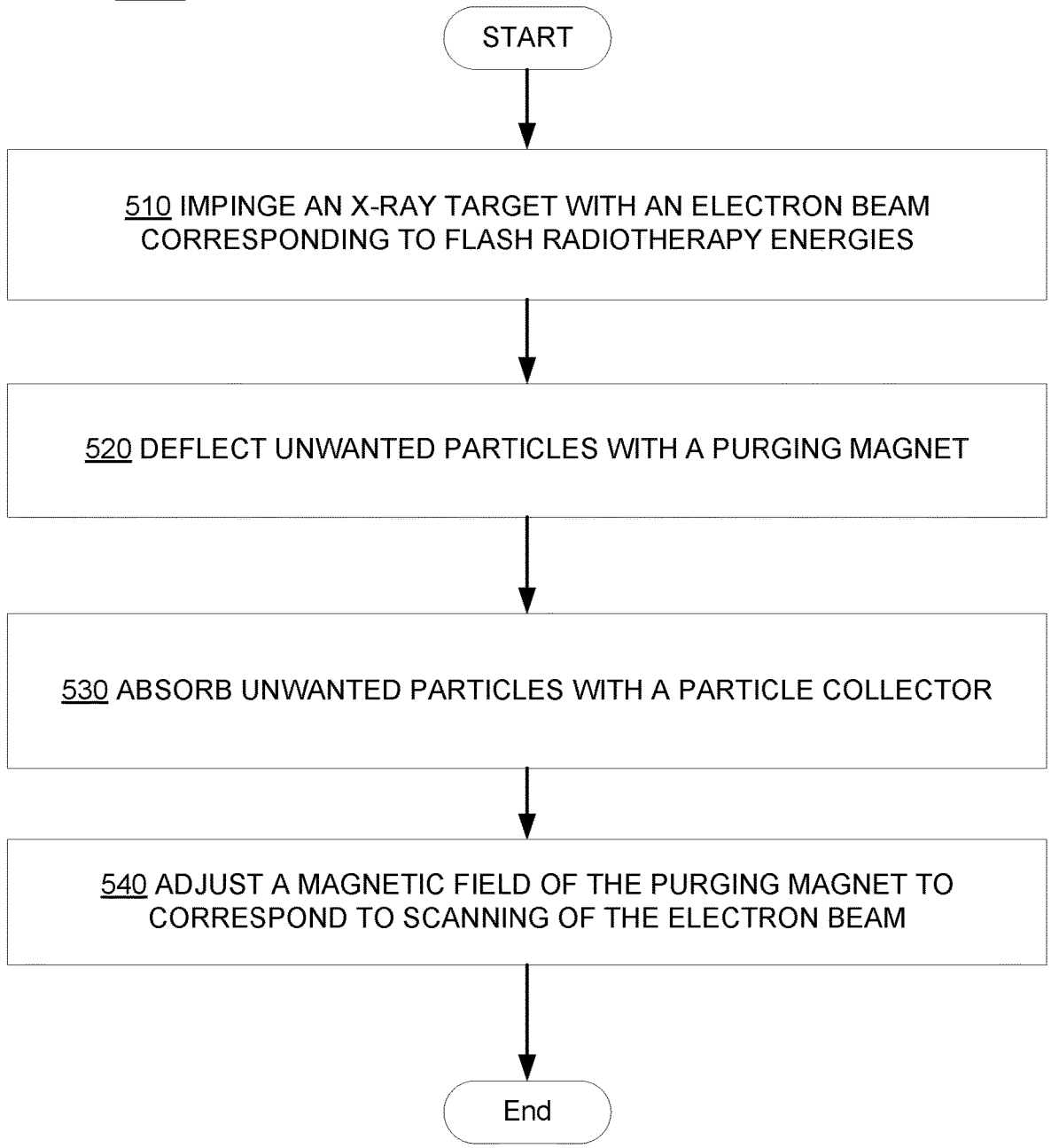
FIG. 5 illustrates an exemplary method of generating a FLASH radiotherapy beam, in accordance with embodiments of the present invention.

FIG. 5 illustrates an exemplary method 500 of generating a FLASH radiotherapy beam, in accordance with embodiments of the present invention. In 510, an electron beam, e.g., electron beam 45 (FIG. 1) corresponding to FLASH radiotherapy energies, e.g., 50 MeV, impinges an X-ray target, e.g., X-ray target 50 (FIG. 2). A first portion of electrons of the electron beam collide with particles of the X-ray target to generate X-rays. A second portion of electrons of the electron beam pass through the X-ray target. These electrons are unwanted particles.

In 520, the unwanted particles are deflected or redirected out of the therapeutic X-ray beam path by a purging magnet, e.g., purging magnet 230 (FIG. 2). In 530, the unwanted particles are absorbed by a particle collector, e.g., particle collector 240 (FIG. 2).

In optional 540, a magnetic field of the purging magnet, e.g., purging magnet 230 (FIG. 2) is adjusted or changed to correspond to scanning of the electron beam, e.g., electron beam 45 (FIG. 1).

Figure 6:
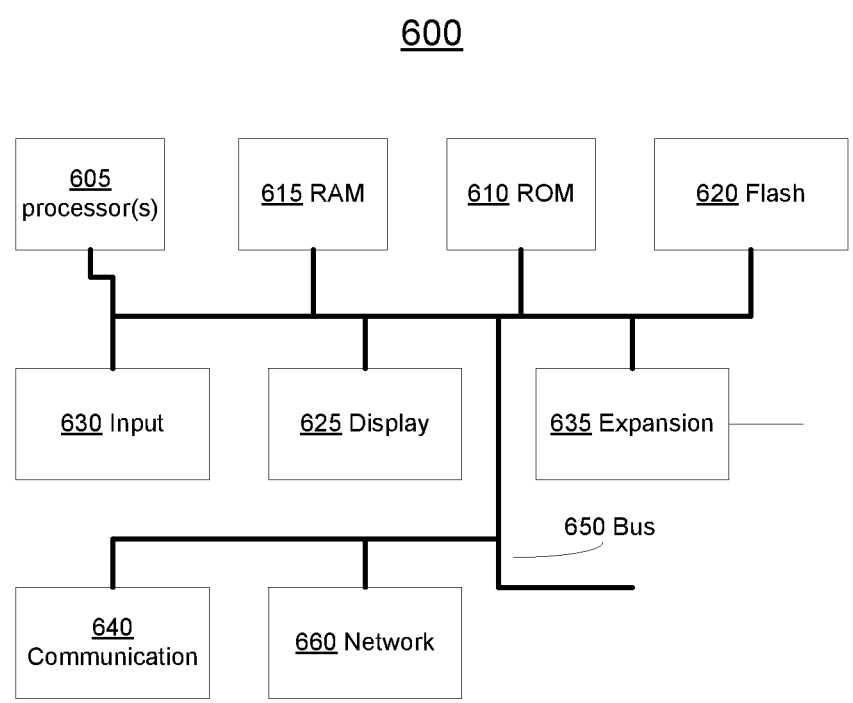
FIG. 6 illustrates a block diagram of an exemplary electronic system 600, which may be used as a platform to implement and/or as a control system for embodiments of the present invention. Electronic

FIG. 6 illustrates a block diagram of an exemplary electronic system 600, which may be used as a platform to implement and/or as a control system for embodiments of the present invention. Electronic system 600 may control various elements of radiation treatment system 100 to beneficially deliver therapeutic radiation to a patient. For example, electronic system 600 may control generation of electrons by linear accelerator 40. Electronic system 600 may also control scanning of an electron beam via scanning magnets, e.g., bending plane scan magnets 47 (FIG. 1) and/or cross plane scanning magnets 201 (FIG. 2). Electronic system 600 may further control multiple aspects of a purging magnet, e.g., purging magnet 230 (FIG. 2), for example, to correspond with operations of scanning magnets.

Electronic system 600 may be a "server" computer system, in some embodiments. Electronic system 600 includes an address/data bus 650 for communicating information, a central processor complex 605 functionally coupled with the bus for processing information and instructions. Bus 650 may comprise, for example, a Peripheral Component Interconnect Express (PCIe) computer expansion bus, industry standard architecture (ISA), extended ISA (EISA), Micro-Channel, Multibus, IEEE 796, IEEE 1196, IEEE 1496, PCI, Computer Automated Measurement and Control (CAMAC), MBus, Runway bus, Compute Express Link (CXL), and the like.

Central processor complex 605 may comprise a single processor or multiple processors, e.g., a multi-core processor, or multiple separate processors, in some embodiments. Central processor complex 605 may comprise various types of well-known processors in any combination, including, for example, digital signal processors (DSP), graphics processors (GPU), complex instruction set (CISC) processors, reduced instruction set (RISC) processors, and/or very long word instruction set (VLIW) processors. In some embodiments, exemplary central processor complex 605 may comprise a finite state machine, for example, realized in one or more field programmable gate array(s) (FPGA), which may operate in conjunction with and/or replace other types of processors to control embodiments in accordance with the present invention.

Electronic system 600 may also include a volatile memory 615 (e.g., random access memory RAM) coupled with the bus 650 for storing information and instructions for the central processor complex 605, and a non-volatile memory 610 (e.g., read only memory ROM) coupled with the bus 650 for storing static information and instructions for the processor complex 605. Electronic system 600 also optionally includes a changeable, non-volatile memory 620 (e.g., NOR flash) for storing information and instructions for the central processor complex 605 which can be updated after the manufacture of system 600. In some embodiments, only one of ROM 610 and/or Flash memory 620 may be present.

Also included in electronic system 600 of FIG. 6 is an optional input device 630. Input device 630 can communicate information and command selections to the processor complex 605. Input device 630 may be any suitable device for communicating information and/or commands to the electronic system 600. For example, input device 630 may take the form of a keyboard, buttons, a joystick, a track ball, an audio transducer, e.g., a microphone, a touch sensitive digitizer panel, eyeball scanner, and/or the like.

Electronic system 600 may comprise a display unit 625. Display unit 625 may comprise a liquid crystal display (LCD) device, cathode ray tube (CRT), field emission device (FED, also called flat panel CRT), light emitting diode (LED), plasma display device, electro-luminescent display, electronic paper, electronic ink (e-ink) or other display device suitable for creating graphic images and/or alphanumeric characters recognizable to the user. Display unit 625 may have an associated lighting device, in some embodiments.

Electronic system 600 also optionally includes an expansion interface 635 coupled with the bus 650. Expansion interface 635 can implement many well known standard expansion interfaces, including without limitation the Secure Digital Card interface, universal serial bus (USB) interface, Compact Flash, Personal Computer (PC) Card interface, CardBus, Peripheral Component Interconnect (PCI) interface, Peripheral Component Interconnect Express (PCI Express), mini-PCI interface, IEEE 1394, Small Computer System Interface (SCSI), Personal Computer Memory Card International Association (PCMCIA) interface, Industry Standard Architecture (ISA) interface, RS-232 interface, and/or the like. In some embodiments of the present invention, expansion interface 635 may comprise signals substantially compliant with the signals of bus 650.

A wide variety of well-known devices may be attached to electronic system 600 via the bus 650 and/or expansion interface 635. Examples of such devices include without limitation rotating magnetic memory devices, flash memory devices, digital cameras, wireless communication modules, digital audio players, and Global Positioning System (GPS) devices.

System 600 also optionally includes a communication port 640. Communication port 640 may be implemented as part of expansion interface 635. When implemented as a separate interface, communication port 640 may typically be used to exchange information with other devices via communication-oriented data transfer protocols. Examples of communication ports include without limitation RS-232 ports, universal asynchronous receiver transmitters (UARTs), USB ports, infrared light transceivers, ethernet ports, IEEE 1394, and synchronous ports.

System 600 optionally includes a network interface 660, which may implement a wired or wireless network interface. Electronic system 600 may comprise additional software and/or hardware features (not shown) in some embodiments.

Various modules of system 600 may access computer readable media, and the term is known or understood to include removable media, for example, Secure Digital ("SD") cards, CD and/or DVD ROMs, diskettes and the like, as well as non-removable or internal media, for example, hard drives, solid state drive s (SSD), RAM, ROM, flash memory, and the like.

Embodiments in accordance with the present invention provide systems and methods for high dose rate radiotherapy. In addition, embodiments in accordance with the present invention provide systems and methods for high dose rate radiotherapy that remain reliable in response to the high energy levels of FLASH radiotherapy. Further, embodiments in accordance with the present invention provide systems and methods for high dose rate electron beam therapy that allow for scanning of a radiotherapy beam. Still further, embodiments in accordance with the present invention provide systems and methods for high dose rate electron beam therapy that allow for scanning of a radiotherapy beam.

Although the invention has been shown and described with respect to a certain exemplary embodiment or embodiments, equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

Various embodiments of the invention are thus described. While the present invention has been described in particular embodiments, it should be appreciated that the invention should not be construed as limited by such embodiments, but rather construed according to the below claims.

I claim:

1. A radiotherapy system comprising:
an X-ray target configured to convert an incident electron beam into an X-ray beam, wherein the X-ray beam delivers a radiation rate of greater than or equal to 40 grays per second;
a purging magnet configured to redirect unwanted particles emitted from said X-ray target away from said X-ray beam; and
a particle collector configured to absorb said unwanted particles subsequent to a redirection by said purging magnet.

2. The radiotherapy system of claim 1, wherein said particle collector is configured to dissipate at least 50% of an energy of said incident electron beam.

3. The radiotherapy system of claim 1, wherein said X-ray target is less than 3.5 mm thick.

4. The radiotherapy system of claim 1, wherein said X-ray target comprises metals having an atomic number greater than or equal to 42.

5. The radiotherapy system of claim 1, wherein said X-ray target comprises tungsten (W).

6. The radiotherapy system of claim 1, wherein said X-ray target is configured to dissipate less than 25% of an energy of said incident electron beam.

7. The radiotherapy system of claim 1, wherein said particle collector is configured to dissipate at least 75% of an energy of said incident electron beam.

8. The radiotherapy system of claim 1, wherein said particle collector comprises materials having an atomic number less than 42.

9. The radiotherapy system of claim 8, wherein said particle collector comprises a cladding including X-ray absorptive materials.

10. The radiotherapy system of claim 1, wherein said incident electron beam comprises an electron energy of at least 50 MeV.

11. The radiotherapy system of claim 1, wherein said X-ray target is configured to rotate through said incident electron beam.

12. A radiotherapy system configured for a FLASH radiotherapy, said radiotherapy system comprising:
  a bremsstrahlung X-ray target configured to convert a portion of a stream of electrons into X-rays;
  a purging magnet configured to redirect particles escaping from said bremsstrahlung X-ray target while passing said X-rays; and
  a particle collector configured to absorb said escaping particles subsequent to a redirection by said purging magnet.

13. The radiotherapy system of claim 12, further comprising:
  a linear accelerator configured to accelerate the stream of electrons to an energy of at least 50 MeV.

14. The radiotherapy system of claim 12, further comprising:
  a plurality of scanning magnets configured to adjust a location of said stream of electrons.

15. The radiotherapy system of claim 14, wherein said plurality of scanning magnets are configured to modify a beam profile of said X-rays.

16. The radiotherapy system of claim 14, wherein said purging magnet is configured to adjust to changes in a location of said stream of electrons due to actions of said plurality of scanning magnets.

17. The radiotherapy system of claim 12, wherein said bremsstrahlung X-ray target comprises metals having an atomic number greater than or equal to 42.

18. The radiotherapy system of claim 12, wherein said particle collector comprises materials having an atomic number less than 42.

19. The radiotherapy system of claim 12, wherein said particle collector comprises a cladding including X-ray absorptive materials.

20. The radiotherapy system of claim 12, wherein said particle collector is configured to absorb at least four times as much energy from said stream of electrons in comparison to energy absorbed by said bremsstrahlung X-ray target.

21. The radiotherapy system of claim 12, wherein said particle collector comprises internal cooling channels configured for a cooling liquid to remove heat from said particle collector.

22. The radiotherapy system of claim 12, wherein said particle collector is configured to absorb and dissipate at least 20 kilowatts of power from said escaping particles.

23. A method of operating a radiotherapy system, the method comprising:
  impinging an electron beam on an X-ray target to generate an X-ray beam, wherein said X-ray target includes metals having an atomic number greater than or equal to 42;
  redirecting unwanted particles out of the X-ray beam by a purging magnet; and
  absorbing said unwanted particles by a particle collector, wherein said particle collector includes materials having an atomic number less than 42.

24. The method of claim 23, further comprising:
  adjusting a magnetic field of said purging magnet to correspond to scanning of said electron beam.

* * * * *